(12) United States Patent
Taha et al.

(10) Patent No.: US 6,597,943 B2
(45) Date of Patent: Jul. 22, 2003

(54) METHOD OF USING SPECTRAL MEASURES TO DISTINGUISH AMONG ATRIALFIBRILLATION, ATRIAL-FLUTTER AND OTHER CARDIAC RHYTHMS

(75) Inventors: Basel Taha, Menomonee Falls, WI (US); Shankara Reddy, Cedarburg, WI (US); Joel Xue, Germantown, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 301 days.

(21) Appl. No.: 09/748,462

(22) Filed: Dec. 26, 2000

(65) Prior Publication Data

US 2002/0120206 A1 Aug. 29, 2002

(51) Int. Cl.[7] ............................................. A61B 5/046
(52) U.S. Cl. ........................................ 600/515; 600/518
(58) Field of Search ................................. 600/515, 518, 600/521; 607/5, 14

(56) References Cited

U.S. PATENT DOCUMENTS

| | | | | | |
|---|---|---|---|---|---|
| 5,092,341 | A | * | 3/1992 | Kelen | 600/508 |
| 5,109,862 | A | * | 5/1992 | Kelen et al. | 600/515 |
| 5,609,158 | A | * | 3/1997 | Chan | 600/518 |
| 6,192,273 | B1 | * | 2/2001 | Igel et al. | 607/14 |
| 6,490,478 | B1 | * | 12/2002 | Zhang et al. | 600/518 |

* cited by examiner

*Primary Examiner*—Jeffrey R. Jastrzab
(74) *Attorney, Agent, or Firm*—Welsh & Katz, Ltd.

(57) ABSTRACT

A method and apparatus are provided for differentiating among atrial-flutter, atrial-fibrillation and other cardiac rhythms. The method includes the steps of estimating a spectral entropy of atrial cardiac activity from an electrocardiogram of a patient and determining that the patient has atrial fibrillation when the spectral entropy is greater than a predetermined value.

33 Claims, 7 Drawing Sheets

EXAMPLE 1:

ECG LEADS BEFORE QRST SUBTRACTION

EXAMPLE 1

AFTER QRST SUBTRACTION P-WAVES ARE LEFT IN THE RESIDUAL SIGNAL.

EXAMPLE 2:

BEFORE QRST SUBSTRACTION

EXAMPLE 2:

AFTER QRST SUBSTRACTION ARTRIAL AVTIVITY REMAINING

EXAMPLE 2:
   AFTER BP FILTERING, THIS IS WHAT THE SPECTRAL ANALYSIS IS APPLIED ON.

METHOD OF USING SPECTRAL MEASURES TO DISTINGUISH AMONG ATRIAL FIBRILLATION, ATRIAL-FLUTTER AND OTHER CARDIAC RHYTHMS

FIELD OF THE INVENTION

The field of the invention relates to cardiac monitoring and more particularly to methods of distinguishing between different types of cardiac abnormalities.

BACKGROUND OF THE INVENTION

Atrial fibrillation (AFIB) and atrial flutter (AFL) are two of the most common abnormal cardiac rhythms, constituting up to 8% of electrocardiograms (ECGs) collected by hospitals. The two rhythms have clinically different implications and require different management. In addition, fibrillatory and flutter waves have different generating mechanisms in the atria. However, these two rhythms are often cross classified by physicians and by computerized ECG analysis systems for two main reasons. First, patterns of atrial flutter and fibrillation often coexist within the same ECG segment examined. The second cause of cross-classification is due to the difficulty of detecting atrial activity (visually or by computer time-based analysis) due to the overlying (and dominant) waveforms of ventricular origin (i.e., the QRS complex and T-wave), especially in the case of high ventricular rates.

SUMMARY

A method and apparatus are provided for differentiating among atrial-flutter, atrial-fibrillation and other cardiac rhythms. The method includes the steps of estimating a spectral entropy of atrial cardiac activity from an electrocardiogram of a patient and determining that the patient has atrial fibrillation when the spectral entropy is greater than a predetermined value.

DETAILED DESCRIPTION OF A PREFERRED EMBODIMENT

Figure 1:
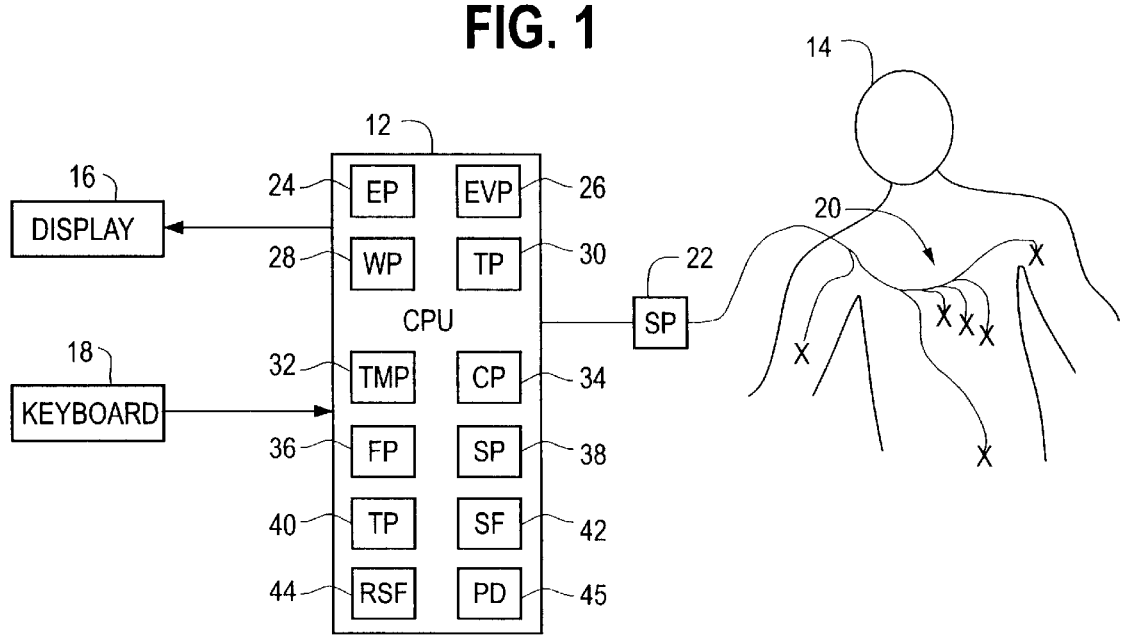
FIG. 1 depicts a system 10 that may be used for analysis of cardiac abnormalities in accordance with an illustrated embodiment of the invention.

FIG. 1 is a block diagram of a system 10, shown generally under an illustrated embodiment of the invention, for differentiating among atrial flutter (AFL), atrial fibrillation (AFIB) and other cardiac rhythms. An operator (not shown) may operate the system 10 based upon control commands entered through a keyboard 18 and view results through a display 16.

Figure 8:
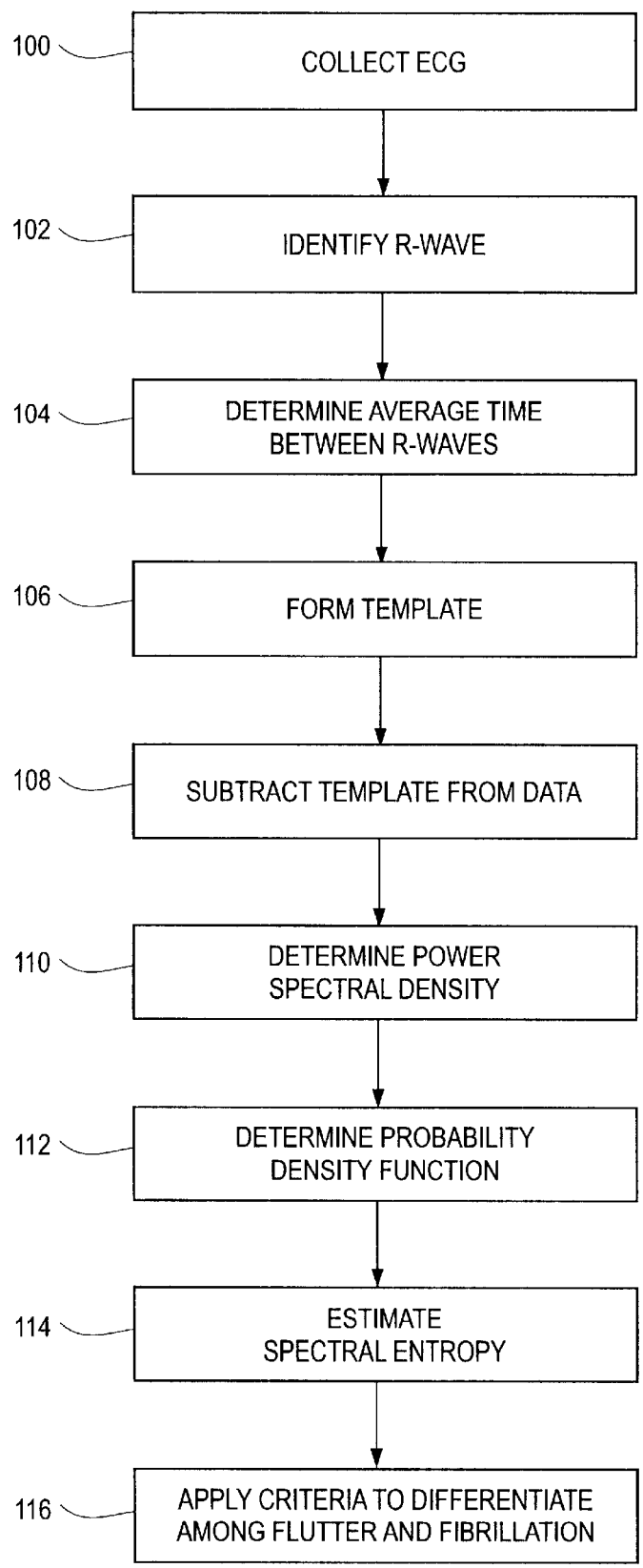
FIG. 8 is a flow chart of process steps that may be followed by the system of FIG. 1.

FIG. 8 is a flow chart of method steps that may be used by the system 10 in differentiating among atrial flutter (AFL), atrial fibrillation (AFIB) and other cardiac rhythms. Reference shall be made to FIG. 8 as appropriate to an understanding of the invention.

As shown, a series of heart monitoring lead wires 20 may be connected to a number of electrocardiograph data collection sites (e.g., left arm, right arm, left leg, right leg, V1–V6) on a body 14 of a patient. A sampling processor 22 may collect voltage samples 100 from each of the wires 20 at an appropriate sampling rate (e.g., 500 samples per second (sps)). A central processing unit (CPU) 12 may collect the samples and store the samples of the ECG in a cardiac sample file 42 for processing.

Within the CPU 12, a spectral entropy processor 24 may be used in conjunction with an evaluation processor 26 to provide a reliable indication of atrial function. The spectral entropy processor 24 may generate an objective measure of the spectral entropy of detected electrical activity of the atria. The evaluation processor may compare this objective measure of electrical activity with predetermined criteria which, as described below, provide a reliable means for differentiating between AFL, AFIB and other forms of cardiac activity.

QRST subtraction may be used to help isolate atrial rhythms. Under this technique, a median waveform of the P-QRS-T pattern may be generated for each recorded lead. Subsequently, the QRS-T portion of the median (from QRS onset to T offset) is time-aligned and subtracted from the original data, leaving the atrial activity as a residual signal.

Frequency domain techniques may then be used on the residual QRST-subtracted signals to distinguish between atrial fibrillation and atrial flutter. More specifically, a determination may be made of the spectral entropy (SE) within the residual signals. The SE may be used as a measure of the stochastic complexity of a signal and to indicate the level of organization of atrial activity. AFIB, whose pathogenesis may involve multiple circulatory pathways within the atria (i.e., a large number of processes) has been found to generate higher SE values. Conversely, AFL has been found to have lower SE values since it is generated by a singular source within the atria. Automated detection of dominant spectral peaks may be used to gauge the frequency content of the residual signals.

Turning now to the system 10, an example will be provided of the techniques used in the collection and analysis of a specific patient. Following the example, a summary will be provided of the comparative results of the analysis of many patients.

Under an illustrated embodiment, the operator may initiate an electrocardiograph by the entry of specific commands through the keyboard 18. In response, the CPU 12 and signal processor (SP) 22 may begin to collect readings 100 from the leads 20 for an appropriate time period (e.g., 10 seconds). An analog to digital (A/D) converter (not shown) within the SP 22 may convert the analog data into a digital format.

Within the CPU 12, the data may be processed immediately, or stored in a set of sample files (SFs) 42 for later processing. In either case, a waveform processor (WP) 28 may be used to generate a median waveform (i.e., a template) 50 (FIG. 2) of the cardiac cycle.

Figure 2:
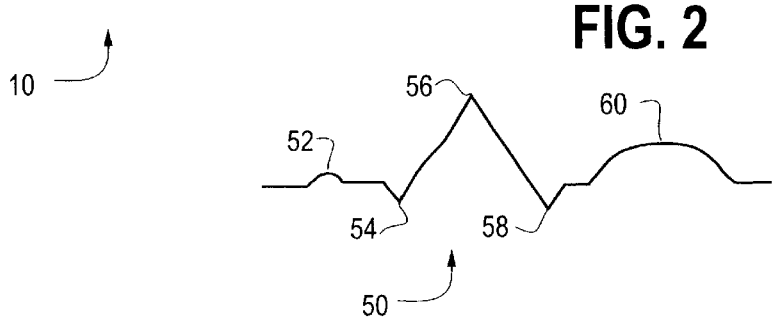
FIG. 2 depicts an electrocariographic profile of a cardiac cycle that may be processed by the system of FIG. 1.

The template 50 of FIG. 2 may be regarded as representative (i.e., an average) of many cardiac cycles, which have been sampled through a particular lead of the leads 20 and stored as part of the ECG. As shown, a cardiac cycle 50 may include a P-wave 52, Q-wave 54, R-wave 56, S-wave 58 and T-wave 60.

While the template 50 has a specific appearance which is suggestive of the particular lead 20 from which it may have been collected, it should be understood that similar waveforms of the P-QRS-T complex may be collected from each of the eight leads I, II, V1–V6.

It should also be understood that signal processing from the eight leads 20 may be accomplished in parallel. A template 50 may be created from a source waveform detected on each lead 20. The template 50 may then be subtracted from the sample data of the lead to create a separate residual sample file (RSF) 44 for each lead. A composite SE may be determined from the residual files.

To create the template 50, the WP 28 may first identify 102 the location of the R-wave 56 within each cardiac cycle. (As used herein, the R-wave 50 refers to the peak value of the R-segment of the QRS complex.) The R-wave 56 may be identified by any number of different processes. For example, the WP 28 may identify the rising waveform leading to the R-wave 56 by comparison of sample values with a threshold value. The peak which defines a relative maximum of the R-wave segment may be found by subtracting a previous sample from a current sample and selecting the sample associated with a sign change as the sample defining the location of the R-wave 56.

Once the R-wave 56 has been identified for each heartbeat within the sequence, an average time $t_a$ between heartbeats may be determined 104 within a timing processor 30. Once an average time has been determined, the time value $t_a$ may be used to define a template window around the R-wave. While any number of methods may be used to define the time window, the method used herein places 40% of the average time $t_a$ ahead of the R-wave and 60% after the R-wave.

The window may be used as a reference device for signal processing herein. By placing the window around the R-wave, the R-wave occupies a predetermined position within the window as does every other respective sample before and after the R-wave.

Once the time window has been identified, the respective sample values within the time window of the respective cardiac cycles may be averaged or medianized to form 106 the template 50 within a template processor (TMP) 32 using the identified R-wave as a reference point. For example, the sample value defining each R-wave may be averaged over the time interval of the ECG. Similarly, the respective sample values ahead and behind the identified R-waves may be averaged to define each average sample value of the template 50.

Following creation of the template 50, the P-wave 52, Q-wave 54, R-wave 56, S-wave 58 and T-wave 60 may be identified, if present, within the template 50 using a process similar to that described above. It may be noted in passing that P-waves may not always be found. For example, AFIB and AFL, by definition, would not have P-waves, but rather would have F-waves (flutter or fibrillation).

The template 50 may then be modified to include only the QRST portion. This preserves information relating to atrial processes that may then be used for subsequent analysis.

It may be noted that while the term "averaged" is used herein, the templates may actually be made up of median values. For example, half the values may be above the chosen value and half may be below. A value closest the center may be chosen as the "average value".

The averaged values of the modified template 50 may then be subtracted 108 from the identified cardiac cycles of its source waveform within a comparison processor (CP) 34, again using the identified R-wave as a reference point. The remaining information forms a residual file. As above, the sample information may be processed one sample at a time. The averaged R-wave sample of the template 50 is subtracted from the identified R-wave sample of each heartbeat. The averaged value one sample prior to the R-wave is subtracted from the sample value one sample prior to the identified R-wave of each heartbeat. The process is repeated until each value of the modified template 50 has been subtracted from each respective sample value of the identified heartbeats of the source waveform.

Figure 9:
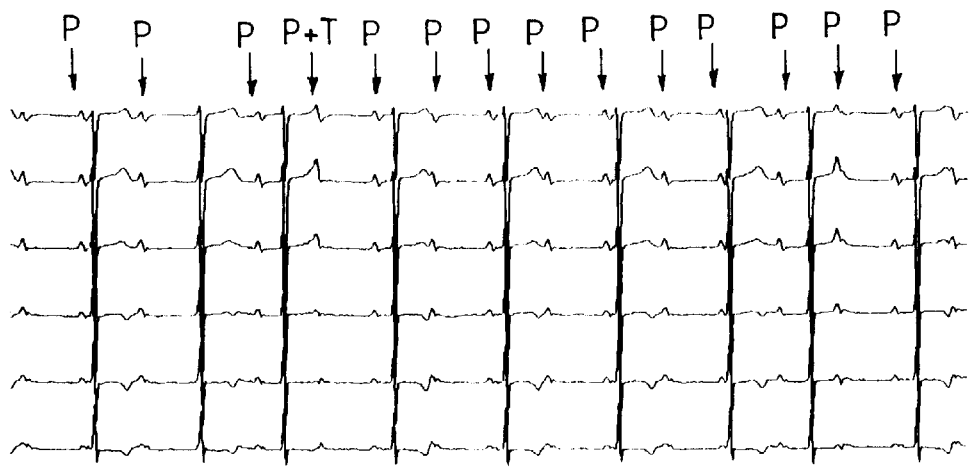
FIGS. 9–10 are a first example of tracings of cardiac activity processing by the system of FIG. 1 before and after QRST subtraction.
Figure 10:
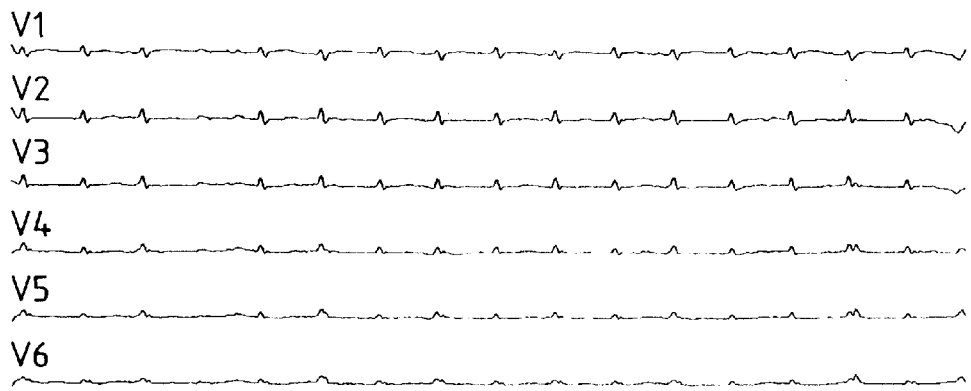
Figure 11:
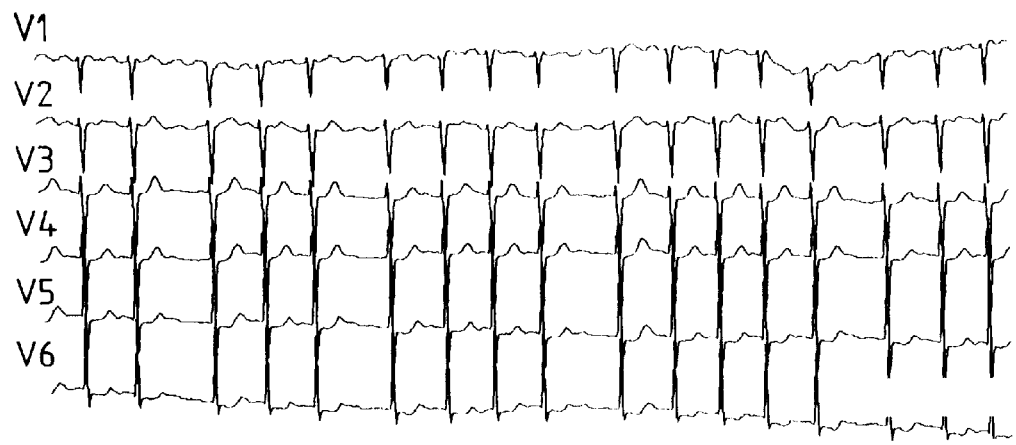
FIGS. 11–13 are a second example of tracings of cardiac activity processing by the system of FIG. 1 before and after QRST subtraction and also after bandpass filtering.
Figure 12:
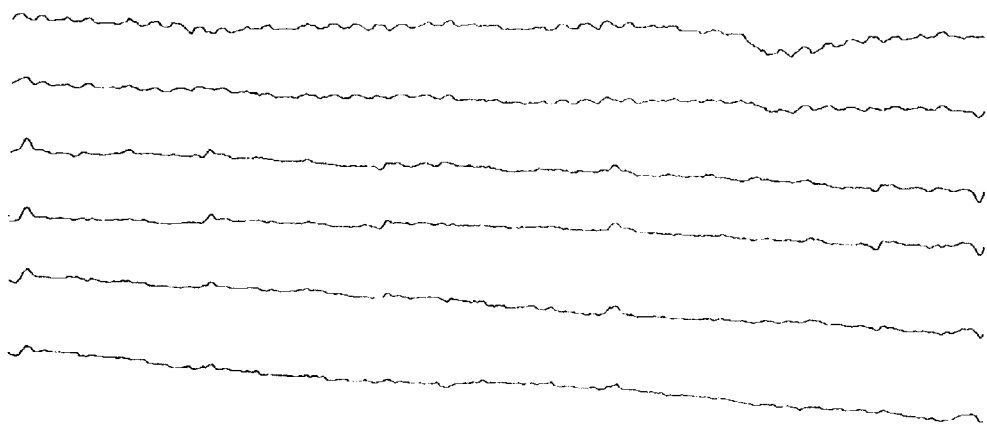
Figure 13:
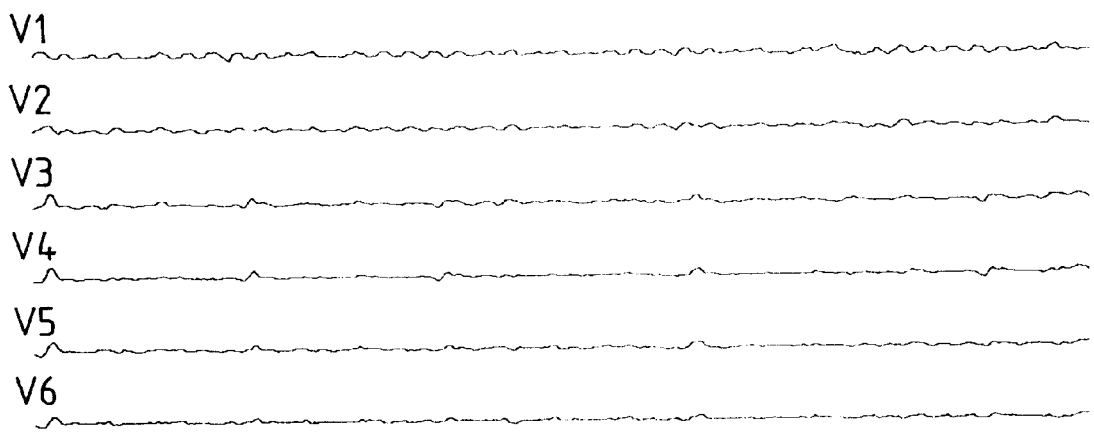

FIGS. 9–13 are examples of initial and processed sample streams. FIGS. 9–10 is an example collected from a first patient. FIGS. 11–13 is a second example from a second patient The six tracings in each of FIGS. 9–13 are sample streams associated with leads V1–V6.

As shown, FIGS. 9 and 11 are ECG lead information before QRST subtraction. FIG. 9 includes a series of P-wave marker arrows along the top margin. FIG. 10 shows the remaining information of FIG. 9 after QRST subtraction. As may be noted, the P-waves shown in FIG. 9 are still present in FIG. 10.

FIG. 11 presents lead information before QRST subtraction. As may be noted, atrial activity is obscured by the dominant ventricular activity in FIG. 11.

FIG. 12 shows the information of FIG. 11, but after QRST subtraction, leaving atrial activity as a residual signal. As may be noted, the tracings slant downward and to the right.

The residual file may then be bandpass filtered to remove noise. Bandpass filtering may be accomplished using a second-order Butterworth filter with a bandpass in an appropriate range (e.g., 1–30 Hz).

FIG. 13 shows the information of FIG. 11 after bandpass filtering. As may be noted, the downward slant of FIG. 12 has been removed by the filtering.

From the filtered residual file (FIGS. 10 and 13), the spectral complexity of the residual file may be determined within a Fourier processor 36. By performing a Fourier transformation of the residual file, a power spectral density $\hat{P}(f)$ of each residual file may be determined 110 using the Welch periodgram method. The power spectral density represents the distribution of power generated by processes occurring within the atria as a function of frequency. Individual power spectra of the residuals of the eight recording leads (i.e., I, II, V1–V6) may then be averaged and normalized with respect to the total spectral power of all the leads to determine 112 a probability density function (pdf). Shannon's channel entropy may then be used to provide an estimate 114 of the spectral entropy (SE) of the atrial processes within a summation processor (SP) 38 as follows:

$$SE = \sum_{f=0}^{f=f_s/2} pdf(f) \times \log\left(\frac{1}{pdf(f)}\right),$$

where f is frequency and $f_s$ is the sampling frequency. A peak detector 45 which relies upon a peak detection algorithm and a moving window segmentation process may be used to detect the dominant peaks in the pdf.

Using the method described above, the process was applied to 4,172 ECGs. Table I is a contingency table showing results among classifications made by the system 10 (shown in Table I as "Sys.") and a cardiologist (shown in Table I as "card."). The sensitivity of the system 10 regarding detection of AFIB and AFL was 79.1% and 80% respectively. Specificity for both rhythms was high (98.8% and 99.5% respectively). Cross-classification error was 5.6%.

TABLE I

|  | Card. AFIB | Card. AFL | Card. Other |
| --- | --- | --- | --- |
| Sys. AFIB | 223 | 8 | 39 |
| Sys. AFL | 10 | 80 | 10 |
| Sys. Other | 49 | 12 | 3741 |

Figure 3:
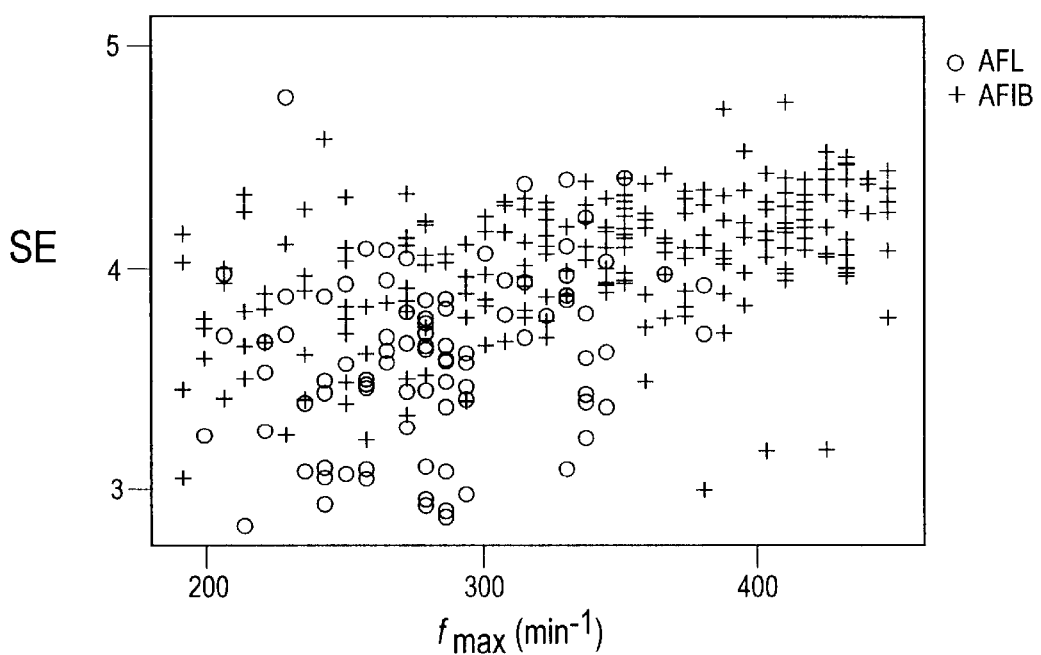
FIG. 3 depicts a scatterplot of spectral entropy (SE) and frequency of maximal power ($f_{max}$) values that may be generated by the system of FIG. 1 for a group of AFL and AFIB rhythms.
Figure 4:
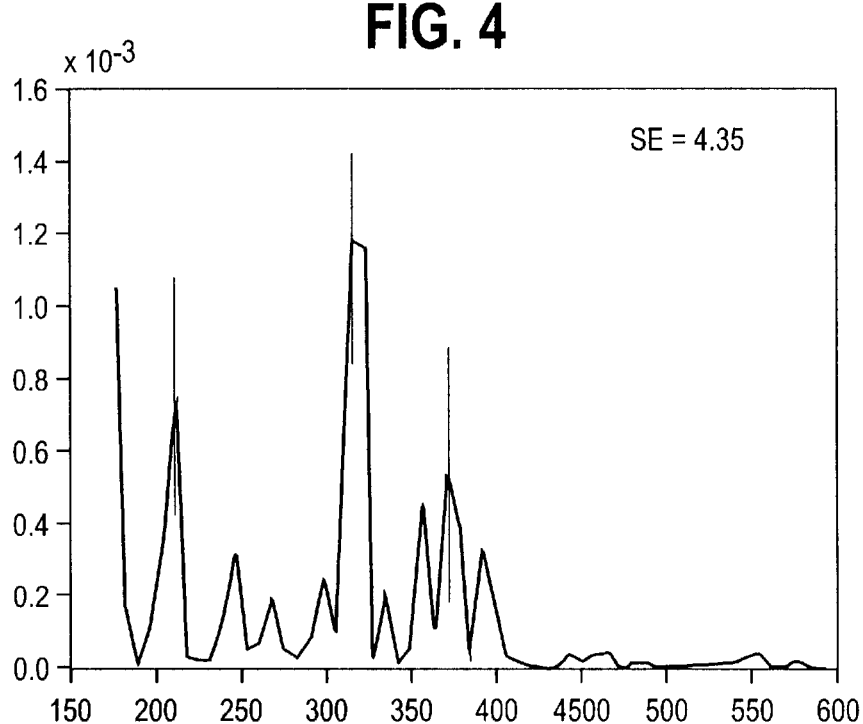
FIGS. 4 and 5 depict exemplary power spectra that may be generated by the system of FIG. 1 showing the spectral complexity of atrial fibrillation.
Figure 5:
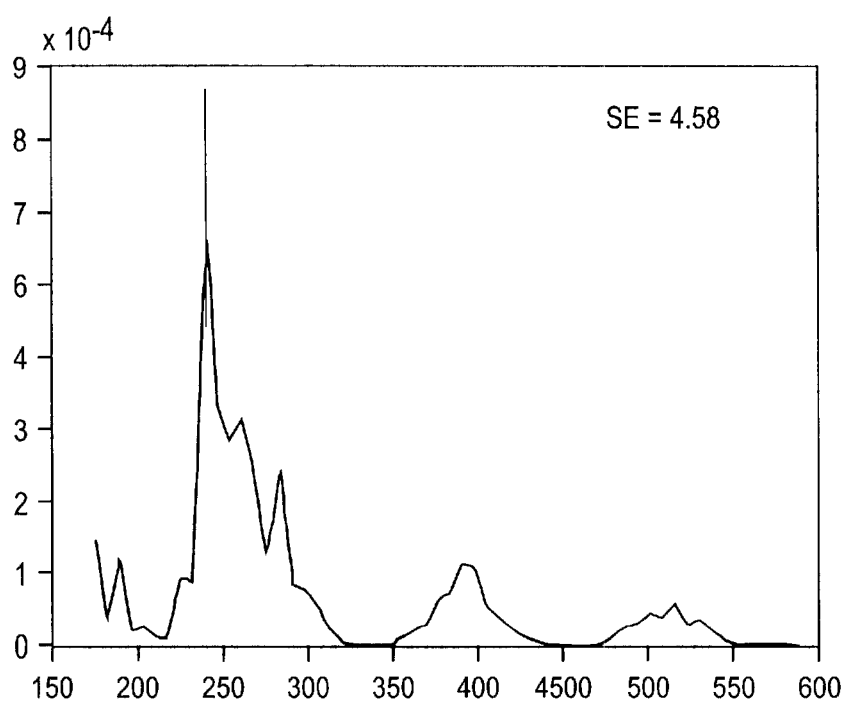
Figure 6:
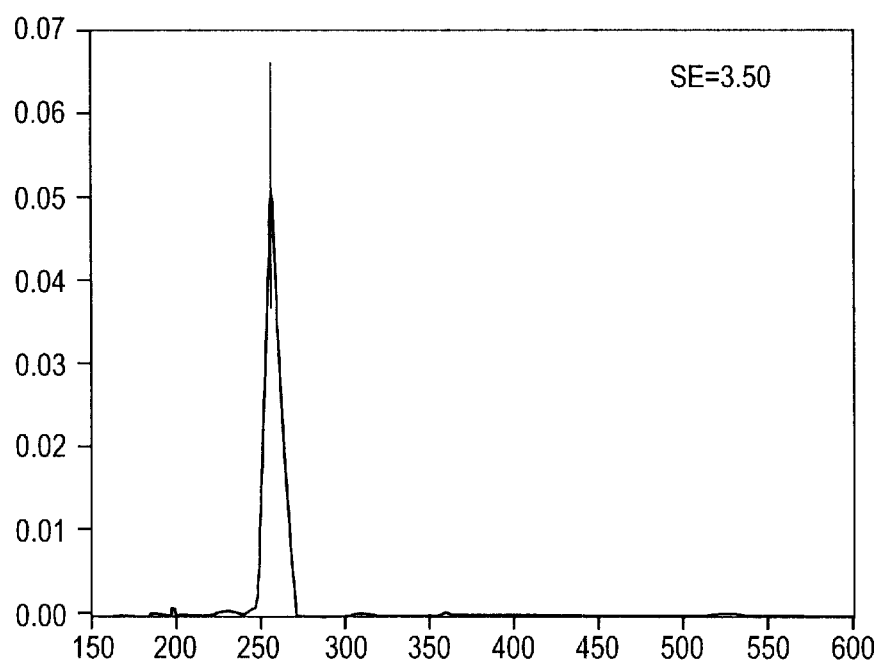
FIGS. 6 and 7 depict the exemplary power spectra that may be generated by the system of FIG. 1 showing the spectral complexity of atrial flutter.
Figure 7:
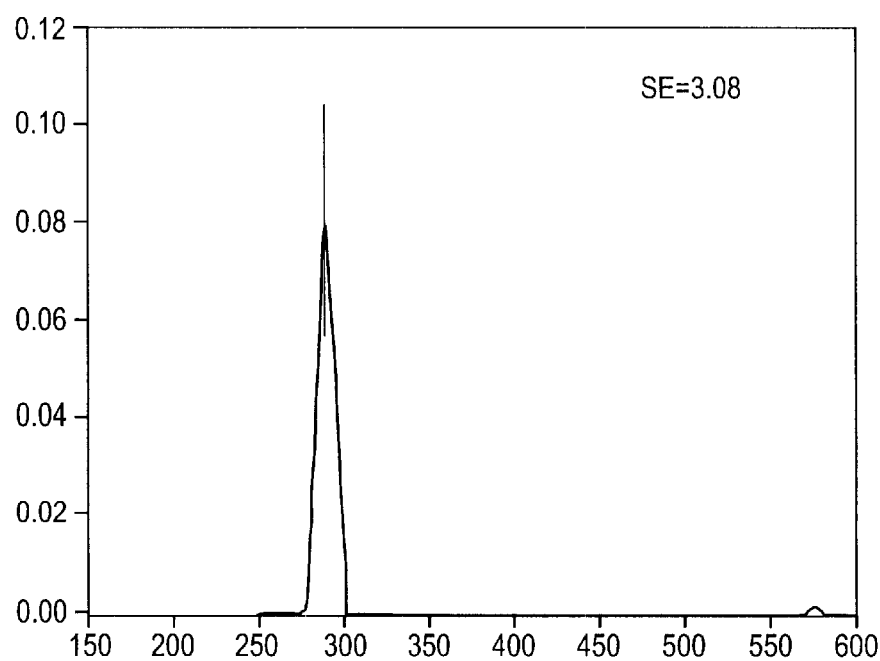

FIG. 3 shows examples of pdfs for 4 ECGs that were cross-classified by established time-based analysis. The spectra for true AFIB ECGs (FIGS. 4–5) are characterized by large SE values and multiple spectral peaks whereas the spectra for true AFL ECGs (FIGS. 6–7) have small SE values and a narrow single peak.

The mean squared SE for AFIB (16.7±2.6, range 8.9 to 25.3) was significantly higher than that for AFL (13.2±2.8, range 8 to 22.8) (p<0.00001). Similarly, the mean maximum dominant frequency of AFIB ECGs (339±72 cpm, range 190 to 447 cpm) was significantly higher than that of AFL ECGs (282±41 cpm, range 198 to 381) (p<0.00001). In spite of these highly significant differences, separation was poor between the two rhythms based on these two measures alone (FIGS. 4–7). This suggests that the spectral measures of the system 10 may be best applied selectively as a post-analysis tool to distinguish AFIB and AFL in ECGs that already show evidence of either rhythm based on established time-based criteria. This strategy has the added advantage of performing the spectral estimation, which is computationally intensive, on only a small subset of hospital ECGs, namely those with pre-existing evidence of either fibrillatory or flutter activity.

The following criteria may be applied 116 within a threshold processor (TP) 40 as an indication of AFIB or AFL after satisfaction of the time-based criteria. For ECGs showing evidence of AFIB, if SE was less than 3.75 with moderately high confidence in p-wave detection (as indicated by a composite score index (Reddy et al. "Computers in Cardiology", IEEE computer Society Press, 1994)), or if there is a single dominant peak below 300 cpm, then the ECG may be found to be AFL. Conversely, for ECGs satisfying the time-based criteria of AFL, if the SE was greater than 4 with a moderately low p-wave detection score, or if there were multiple peaks in the pdf, then the ECG may be found to be AFIB. Applying these frequency-based criteria to 4,172 ECGs results in a reduction in the cross-classification error between AFIB and AFL of from 5.6% to 2.5%. This improvement is statistically significant ($\chi^2$= 4.008, p<0.05).

The results demonstrate the significant advantage of using spectral methods within the system 10 to gain additional insight into the underlying rhythm-generating processes of the atria. However, if used alone, spectral measures may provide less than adequate separation between AFL and AFIB patterns. Significant improvement in distinguishing among these patterns may be achieved through the combination of these measures with other time-based measures.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of differentiating among atrial-flutter, atrial-fibrillation and other cardiac rhythms, such method comprising the steps of:

forming a residual file by subtracting a template heartbeat from each heartbeat of an electrocardiogram of a patient;

estimating a spectral entropy of atrial cardiac activity from the residual file; and determining that the patient has atrial fibrillation when the spectral entropy is greater than a predetermined value.

2. The method of differentiating among atrial-flutter, atrial-fibrillation and other cardiac rhythms as in claim 1 wherein the step of determining that the patient has atrial fibrillation further comprises determining that a probability density function of the spectral density has a plurality of dominant frequencies.

3. The method of differentiating among atrial-flutter, atrial-fibrillation and other cardiac rhythms as in claim 1 further comprising recording the electrocardiogram as a cardiac sample file by sampling a cardiac activity of the patient over a sampling interval.

4. The method of differentiating among atrial-flutter, atrial-fibrillation and other cardiac rhythms as in claim 3 further comprising identifying a temporal location of a plurality of R-waves within a plurality of QRS complexes of a heartbeat of the patient within the cardiac sample file over the sampling interval.

5. The method of differentiating among atrial-flutter, atrial-fibrillation and other cardiac rhythms as in claim 4 further comprising determining an average temporal distance between successive R-waves identified within the QRS complex of the heartbeat of the patient over the sampling interval.

6. A method of differentiating among atrial-flutter, atrial-fibrillation and other cardiac rhythms, such method comprising the steps of:

recording an electrocardiogram of a patient as a cardiac sample file by sampling a cardiac activity of the patient over a sampling interval;

identifying a temporal location of a plurality of R-waves within a plurality of QRS complexes of a heartbeat of the patient within the cardiac sample file over the sampling interval;

determining an average temporal distance between successive R-waves identified within the QRS complex of the heartbeat of the patient over the sampling interval;

forming a template of the QRS complex and T-wave by averaging respective sample values ahead of and behind the identified R-wave estimating a spectral entropy of atrial cardiac activity from the electrocardiogram of a patient; and determining that the patient has atrial fibrillation when the spectral entropy is greater than a predetermined value.

7. The method of differentiating among atrial-flutter, atrial-fibrillation and other cardiac rhythms as in claim 6 further comprising creating a residual cardiac sample file by subtracting the template of the QRS complex from the plurality of QRS complexes within the cardiac sample file.

8. The method of differentiating among atrial-flutter, atrial-fibrillation and other cardiac rhythms as in claim 7 further comprising determining a power spectral density within the residual cardiac waveform.

9. The method of differentiating among atrial-flutter, atrial-fibrillation and other cardiac rhythms as in claim 8 further comprising determining the spectral entropy of the residual cardiac waveform from the power spectral density.

10. The method of differentiating among atrial-flutter, atrial-fibrillation and other cardiac rhythms as in claim 9 further comprising comparing the spectral entropy with a threshold value.

11. The method of differentiating among atrial-flutter, atrial-fibrillation and other cardiac rhythms as in claim 10 further comprising characterizing the patient as having atrial fibrillation when the spectral entropy exceeds the threshold and atrial flutter when it does not.

12. An apparatus for differentiating among atrial-flutter, atrial-fibrillation and other cardiac rhythms, such apparatus comprising:
  means for forming a residual file by subtracting a template heartbeat from each heartbeat of an electrocardiogram of a patient;
  means for estimating a spectral entropy of atrial cardiac activity from the residual file; and
  means for determining that the patient has atrial fibrillation when the spectral entropy is greater than a predetermined value.

13. The apparatus for differentiating among atrial-flutter, atrial-fibrillation and other cardiac rhythms as in claim 12 wherein the means for determining that the patient has atrial fibrillation further comprises means for determining that a probability density function of the spectral density has a plurality of dominant frequencies.

14. The apparatus for differentiating among atrial-flutter, atrial-fibrillation and other cardiac rhythms as in claim 13 further comprising means for identifying a temporal location of a plurality of R-waves within a plurality of QRS complexes of a heartbeat of the patient within the cardiac sample file over the sampling interval.

15. The apparatus for differentiating among atrial-flutter, atrial-fibrillation and other cardiac rhythms as in claim 14 further comprising means for determining an average temporal distance between successive R-waves identified within the QRS complex of the heartbeat of the patient over the sampling interval.

16. An apparatus for differentiating among atrial-flutter, atrial-fibrillation and other cardiac rhythms, such apparatus comprising:
  means for recording an electrocardiogram of a patient as a cardiac sample file by sampling a cardiac activity of the patient over a sampling interval;
  means for identifying a temporal location of a plurality of R-waves within a plurality of QRS complexes of a heartbeat of the patient within the cardiac sample file over the sampling interval;
  means for determining an average temporal distance between successive R-waves identified within the QRS complex of the heartbeat of the patient over the sampling interval;
  means for forming a template of the QRS complex and T-wave by averaging respective sample values ahead of and behind the identified R-wave;
  means for estimating a spectral entropy of atrial cardiac activity from the electrocardiogram of the patient; and
  means for determining that the patient has atrial fibrillation when the spectral entropy is greater than a predetermined value.

17. The apparatus for differentiating among atrial-flutter, atrial-fibrillation and other cardiac rhythms as in claim 16 further comprising means for creating a residual cardiac sample file by subtracting the template of the QRS complex from the plurality of QRS complexes within the cardiac sample file.

18. The apparatus for differentiating among atrial-flutter, atrial-fibrillation and other cardiac rhythms as in claim 17 further comprising means for determining a power spectral density within the residual cardiac waveform.

19. The apparatus for differentiating among atrial-flutter, atrial-fibrillation and other cardiac rhythms as in claim 18 further comprising means for determining the spectral entropy of the residual cardiac waveform from the power spectral density.

20. The apparatus for differentiating among atrial-flutter, atrial-fibrillation and other cardiac rhythms as in claim 19 further comprising means for comparing the spectral entropy with a threshold value.

21. The apparatus for differentiating among atrial-flutter, atrial-fibrillation and other cardiac rhythms as in claim 20 further comprising means for characterizing the patient as having atrial fibrillation when the spectral entropy exceeds the threshold and atrial flutter when it does not.

22. The apparatus for differentiating among atrial-flutter, atrial-fibrillation and other cardiac rhythms as in claim 12 further comprising means for recording the electrocardiogram as a cardiac sample file by sampling a cardiac activity of the patient over a sampling interval.

23. An apparatus for differentiating among atrial-flutter, atrial-fibrillation and other cardiac rhythms, such apparatus comprising:
  a residual file formed by subtracting a template heartbeat from each heartbeat of an electrocardiogram of a patient;
  an entropy processor adapted to estimate a spectral entropy of atrial cardiac activity from the residual file; and
  an evaluation processor adapted to determine that the patient has atrial fibrillation when the spectral entropy is greater than a predetermined value.

24. The apparatus for differentiating among atrial-flutter, atrial-fibrillation and other cardiac rhythms as in claim 23 wherein the evaluation processor further comprises a peak detector adapted to determine that a probability density function of the spectral density has a plurality of dominant frequencies.

25. The apparatus for differentiating among atrial-flutter, atrial-fibrillation and other cardiac rhythms as in claim 23 further comprising a sampling processor adapted to create the electrocardiogram by sampling a cardiac activity of the patient over a sampling interval and store the samples within a cardiac sample file.

26. The apparatus for differentiating among atrial-flutter, atrial-fibrillation and other cardiac rhythms as in claim 25 further comprising a waveform processor adapted to identify a temporal location of a plurality of R-waves within a plurality of QRS complexes of a heartbeat of the patient within the cardiac sample file over the sampling interval.

27. The apparatus for differentiating among atrial-flutter, atrial-fibrillation and other cardiac rhythms as in claim 26 further comprising a timing processor adapted to determine an average temporal distance between successive R-waves identified within the QRS complex of the heartbeat of the patient over the sampling interval.

28. An apparatus for differentiating among atrial-flutter, atrial-fibrillation and other cardiac rhythms, such apparatus comprising:
 a sampling processor adapted to create the electrocardiogram by sampling a cardiac activity of a patient over a sampling interval and store the samples within a cardiac sample file;
 a waveform processor adapted to identify a temporal location of a plurality of R-waves within a plurality of QRS complexes of a heartbeat of the patient within the cardiac sample file over the sampling interval;
 a timing processor adapted to determine an average temporal distance between successive R-waves identified within the QRS complex of the heartbeat of the patient over the sampling interval;
 a template processor adapted to form a template of the QRS complex and T-wave by averaging respective sample values ahead of and behind the identified R-wave;
 an entropy processor adapted to estimate a spectral entropy of atrial cardiac activity from an electrocardiogram of a patient; and
 an evaluation processor adapted to determine that the patient has atrial fibrillation when the spectral entropy is greater than a predetermined value.

29. The apparatus for differentiating among atrial-flutter, atrial-fibrillation and other cardiac rhythms as in claim 28 further comprising a comparison processor adapted to create a residual cardiac sample file by subtracting the template of the QRS complex from the plurality of QRS complexes within the cardiac sample file.

30. The apparatus for differentiating among atrial-flutter, atrial-fibrillation and other cardiac rhythms as in claim 29 further comprising a Fourier processor adapted to determine a power spectral density within the residual cardiac waveform.

31. The apparatus for differentiating among atrial-flutter, atrial-fibrillation and other cardiac rhythms as in claim 30 further comprising a summation processor adapted to determine the spectral entropy of the residual cardiac waveform from the power spectral density.

32. The apparatus for differentiating among atrial-flutter, atrial-fibrillation and other cardiac rhythms as in claim 31 further comprising a threshold processor adapted to compare the spectral entropy with a threshold value.

33. A method of differentiating among atrial-flutter, atrial-fibrillation and other cardiac rhythms, such method comprising the steps of:
 forming a residual file by subtracting a template heartbeat from each heartbeat of an electrocardiogram of a patient;
 estimating a power spectral density of atrial electrical activity present within the residual file;
 calculating a spectral entropy from the estimated power spectral density;
 comparing the calculated spectral entropy with a threshold value; and
 determining that the patient has atrial-fibrillation when the compared spectral entropy exceeds the threshold and atrial flutter when the compared spectral entropy does not exceed the threshold.

* * * * *